United States Patent
Wiesner et al.

(10) Patent No.: US 12,333,738 B2
(45) Date of Patent: Jun. 17, 2025

(54) METHODS, SYSTEMS AND COMPUTER READABLE MEDIUMS FOR EVALUATING AND DISPLAYING A BREATHING MOTION

(71) Applicant: Varian Medical Systems International AG, Steinhausen (CH)

(72) Inventors: Stefan Wiesner, Munich (DE); Erwan Guerin, Daettwil (CH); Jon Sebastien Day, Daettwil (CH); Michael Huber, Daettwil (CH)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 449 days.

(21) Appl. No.: 17/854,602

(22) Filed: Jun. 30, 2022

(65) Prior Publication Data

US 2024/0005523 A1    Jan. 4, 2024

(51) Int. Cl.
*G06T 7/246* (2017.01)
*G06T 7/00* (2017.01)
*G06V 10/25* (2022.01)

(52) U.S. Cl.
CPC ............ *G06T 7/246* (2017.01); *G06T 7/0012* (2013.01); *G06V 10/25* (2022.01); *G06T 2207/10081* (2013.01); *G06T 2207/30061* (2013.01)

(58) Field of Classification Search
CPC ....... A61B 8/543; A61B 5/7285; A61B 6/541; A61B 2017/00075; G06T 7/20; G06T 7/11; G06T 7/215; G06T 7/246; G06T 7/0012; G06T 2207/10081; G06T 2207/30061; G06V 10/25
See application file for complete search history.

(56) References Cited

U.S. PATENT DOCUMENTS

| | | | |
|---|---|---|---|
| 2007/0071172 A1 | 3/2007 | Mollus et al. | |
| 2015/0208987 A1* | 7/2015 | Shan | A61B 5/7207 600/407 |
| 2017/0224256 A1* | 8/2017 | Kirenko | A61B 5/113 |
| 2019/0105514 A1 | 4/2019 | Amstutz et al. | |
| 2019/0378329 A1* | 12/2019 | Kiely | G06T 7/0014 |
| 2020/0046302 A1* | 2/2020 | Jacquel | A61B 5/091 |
| 2020/0402245 A1* | 12/2020 | Keraudren | G06T 7/38 |
| 2022/0240790 A1* | 8/2022 | Smit | A61B 5/1135 |

FOREIGN PATENT DOCUMENTS

| | | | | |
|---|---|---|---|---|
| EP | 3533408 A1 * | 9/2019 | | A61B 34/20 |
| EP | 3756728 A1 | 12/2020 | | |
| WO | WO-2005041775 A1 * | 5/2005 | | A61B 6/00 |
| WO | WO-2014020509 A1 * | 2/2014 | | A61B 5/0077 |
| WO | WO-2016/014718 A1 | 1/2016 | | |
| WO | WO-2016058796 A1 * | 4/2016 | | A61B 5/0077 |
| WO | WO-2020/033613 A1 | 2/2020 | | |
| WO | WO-2021083577 A1 * | 5/2021 | | A61B 5/0064 |

OTHER PUBLICATIONS

Geng, *Structured-light 3D surface imaging: a tutorial*, Advances in Optics and Photonics, vol. 3, Issue 2, pp. 128-160 (2011).
U.S. Appl. No. 17/854,581.

* cited by examiner

*Primary Examiner* — Dung Hong
(74) *Attorney, Agent, or Firm* — Harness, Dickey & Pierce, P.L.C.

(57) ABSTRACT

At least one example embodiment provides a method including obtaining surface information of a patient using a camera; determining a motion of the patient based on the surface information; and providing an indicator of a region of interest (ROI) of the patient based on the motion.

12 Claims, 9 Drawing Sheets

METHODS, SYSTEMS AND COMPUTER READABLE MEDIUMS FOR EVALUATING AND DISPLAYING A BREATHING MOTION

TECHNICAL FIELD

One or more example embodiments relate methods, systems and computer readable mediums for evaluating and displaying a breathing motion of a patient.

BACKGROUND

Radiation therapy involves medical procedures that selectively expose certain areas of a human body, such as cancerous tumors, to doses of radiation. The radiation therapy irradiates the targeted biological tissue such that undesirable tissue is destroyed. Radiation has also been-used to obtain images of tissue for diagnostic or treatment purposes.

Normal physiological movement represents a limitation in the clinical planning and delivery of medical procedures to a patient body. Normal physiological movement, such as respiration or heart movement, can cause a positional movement of the body portion undergoing treatment, measurement, or imaging. With respect to radiation therapy, if the radiation beam has been shaped to conform the treatment volume to the exact dimensions of a tumor, then movement of that tumor during treatment could result in the radiation beam not being sufficiently sized or shaped to fully cover the targeted tumoral tissue.

In four-dimensional (4D) imaging (e.g., Computed Tomography (CT)), a reflective marker block may be positioned on the chest of a patient and tracked with an optical camera to assess a breathing cycle of the patient. A 4D CT reconstruction associates each CT slice acquisition with a corresponding respiratory phase during which the acquisition took place. During setup of the patient, a user (e.g., therapist) positions the marker block as a location of the patient's chest that provides a vertical motion during the breathing cycle.

For certain indications like left sided breast tumors, a planning CT is acquired during a deep-inspiration breath hold (DIBH) in order to take advantage of the heart position during inspiration, which permits a lower dose to the heart during treatment delivery.

SUMMARY

The scope of protection sought for various example embodiments is set out by the independent claims. The example embodiments and/or features, if any, described in this specification that do not fall under the scope of the independent claims are to be interpreted as examples useful for understanding various embodiments.

At least some example embodiments simplify motion monitoring (e.g., at a CT scanner or LINAC) by detecting a particular region on a patient surface to extract a respiratory breathing signal, by providing a display of the patient's motion and by providing motion statistics for different regions of the patent surface.

At least some example embodiments provide a visualization/display to a user to evaluate a breathing motion of the patient. Example embodiments remove/reduce the time spent by the user to find a selected motion observation point on the chest of the patient and provides information to the user with respect to a breathing behavior of the patient, e.g., a ratio between breathing induced chest wall motion and abdominal motion.

According to at least one example embodiment, a method includes obtaining surface information of a patient using a camera; determining a motion of the patient based on the surface information; and providing an indicator of a region of interest (ROI) of the patient based on the motion.

According to at least one example embodiment, the providing the indicator includes determining the ROI of the patient based on the motion.

According to at least one example embodiment, the ROI corresponds to an area of the patient having a highest movement value.

According to at least one example embodiment, the obtaining the surface information includes obtaining a first motion signal from a first area of the patient, and obtaining a second motion signal from a second area of the patient, the ROI being based on the first motion signal and the second motion signal.

According to at least one example embodiment, the determining the ROI is based on at least one of a signal-to-noise ratio associated with a first area of the patient, or a contrast-to-noise ratio between a movement in the first area and a static area of the patient.

According to at least one example embodiment, the determining a motion includes providing a first motion map of the patient before displaying the indicator, the first motion map corresponding to measurements in the surface information and changing over time based on the measurements in the surface information.

According to at least one example embodiment, the determining the motion of the patient includes determining an average motion of the patient based on the measurements in the surface information, the average motion being an average vertical change, and the providing the indicator includes displaying an average motion map after displaying the first motion map, the average motion map depicting the average motion of the patient, the average motion map being a static map and the average motion map including the ROI, and displaying the indicator over the ROI of the patient in the average motion map.

According to at least one example embodiment, the surface information is a three-dimensional (3D) point cloud and the displaying the indicator of the ROI of the patient displays the indicator on a two-dimensional (2D) motion map.

According to at least one example embodiment, an apparatus includes processing circuitry configured to cause the apparatus to obtain surface information of a patient using a camera, determine a motion of the patient based on the surface information, and provide an indicator of a region of interest (ROI) of the patient based on the motion.

According to at least one example embodiment, the processing circuitry is configured to cause the apparatus to determine the ROI of the patient based on the motion.

According to at least one example embodiment, the ROI corresponds to an area of the patient having a highest movement value.

According to at least one example embodiment, the processing circuitry is configured to cause the apparatus to obtain a first motion signal from a first area of the patient, and obtain a second motion signal from a second area of the patient, the ROI being based on the first motion signal and the second motion signal.

According to at least one example embodiment, the processing circuitry is configured to cause the apparatus to determine the ROI based on at least one of a signal-to-noise ratio associated with a first area of the patient, or a contrast-to-noise ratio between a movement in the first area and a static area of the patient.

According to at least one example embodiment, the processing circuitry is configured to cause the apparatus to provide a first motion map of the patient before displaying the indicator, the first motion map corresponding to measurements in the surface information and changing over time based on the measurements in the surface information.

According to at least one example embodiment, the processing circuitry is configured to cause the apparatus to determine an average motion of the patient based on the measurements in the surface information, the average motion being an average vertical change, display an average motion map after displaying the first motion map, the average motion map depicting the average motion of the patient, the average motion map being a static map and the average motion map including the ROI, and display the indicator over the ROI of the patient in the average motion map.

According to at least one example embodiment, the surface information is a three-dimensional (3D) point cloud and the displaying the indicator of the ROI of the patient displays the indicator on a two-dimensional (2D) motion map.

BRIEF DESCRIPTION OF THE DRAWINGS

Example embodiments will become more fully understood from the detailed description given herein below and the accompanying drawings, wherein like elements are represented by like reference numerals, which are given by way of illustration only and thus are not limiting of this disclosure.

It should be noted that these figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment and should not be interpreted as defining or limiting the range of values or properties encompassed by example embodiments. The use of similar or identical reference numbers in the various drawings is intended to indicate the presence of a similar or identical element or feature.

DETAILED DESCRIPTION

Various example embodiments will now be described more fully with reference to the accompanying drawings in which some example embodiments are shown.

Detailed illustrative embodiments are disclosed herein. However, specific structural and functional details disclosed herein are merely representative for purposes of describing example embodiments. The example embodiments may, however, be embodied in many alternate forms and should not be construed as limited to only the embodiments set forth herein.

It should be understood that there is no intent to limit example embodiments to the particular forms disclosed. On the contrary, example embodiments are to cover all modifications, equivalents, and alternatives falling within the scope of this disclosure. Like numbers refer to like elements throughout the description of the figures.

While one or more example embodiments may be described from the perspective of a particular device, it should be understood that one or more example embodiments discussed herein may be performed by the one or more processors (or processing circuitry) at the applicable device. For example, according to one or more example embodiments, at least one memory may include or store computer program code, and the at least one memory and the computer program code may be configured to, with at least one processor, cause a device or system to perform the operations discussed herein.

As discussed herein the terminology "one or more" and "at least one" may be used interchangeably.

It will be appreciated that a number of example embodiments may be used in combination.

Figure 1A:
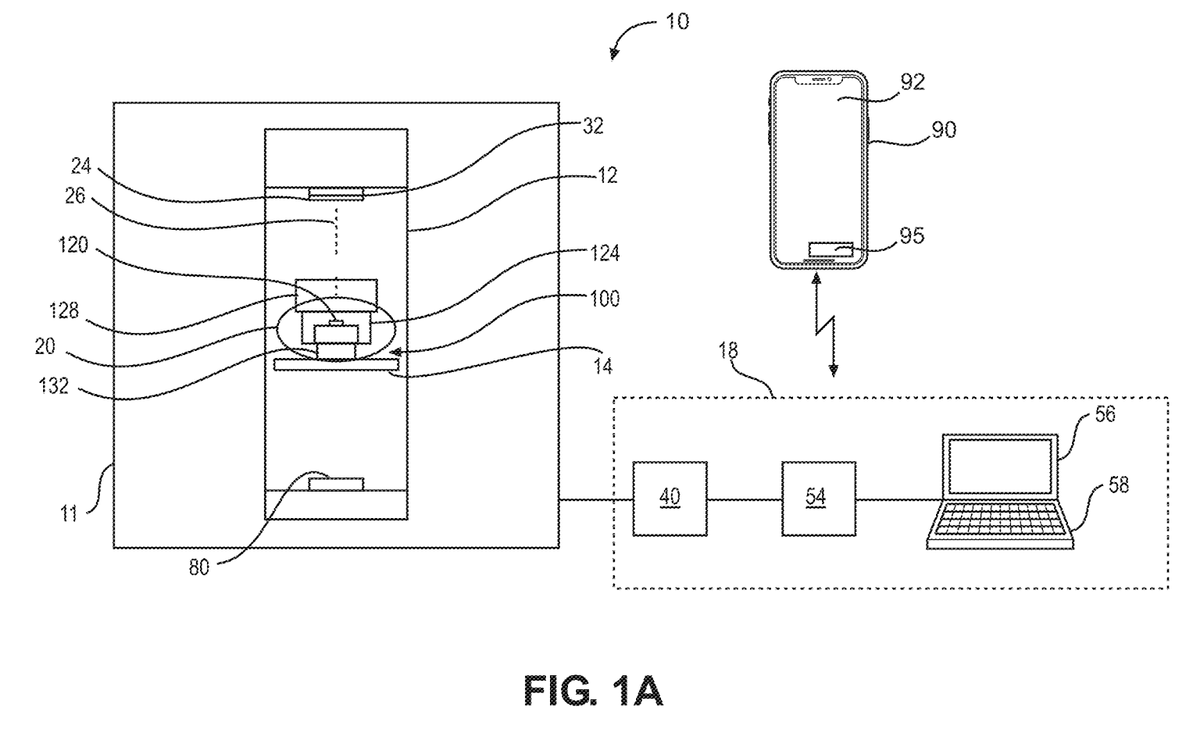
FIGS. 1A-1B illustrate a system according to at least one example embodiment.
Figure 1B:
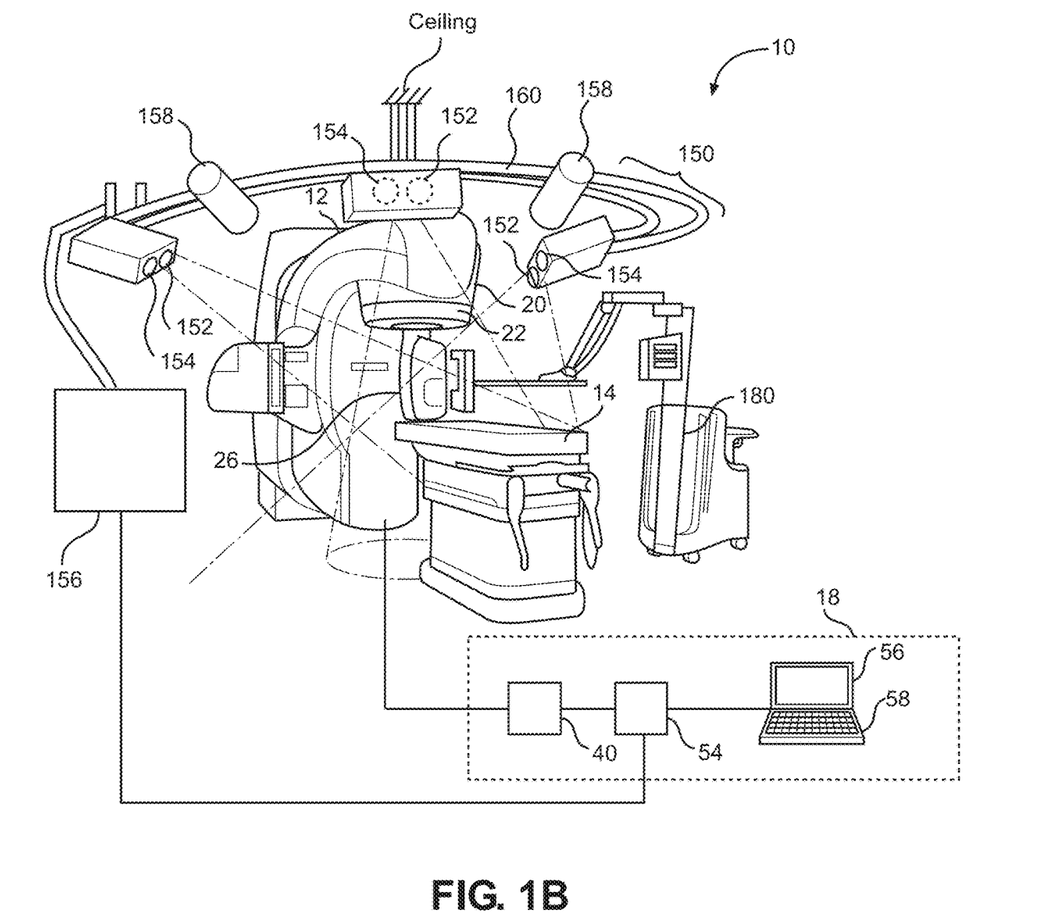

FIGS. 1A-1B illustrate a system according to at least one example embodiment.

FIG. 1A illustrates a medical system 10. In the illustrated embodiment, the medical system 10 is a radiation treatment system, and it includes a medical device 11 and a patient support 14 for supporting a patient 20. The medical device 11 includes an arm gantry 12 and a control system 18 for controlling an operation of the gantry 12 and delivery of radiation. The medical device 11 also includes a radiation source 22 (e.g., a linear accelerator (LINAC)) that projects a beam 26 of radiation towards the patient 20 while the patient 20 is supported on support 14, and a collimator 24 for changing a cross sectional shape of the radiation beam 26. The radiation source 22 may be configured to generate a cone beam, a fan beam, or other types of radiation beams in different embodiments. Also, in other embodiments, the source 22 may be configured to generate proton beam as a form of radiation for treatment purpose. Also, in other embodiments, the system 10 may have other form and/or configuration. For example, in other embodiments, instead of an arm gantry 12, the medical device 11 may have a ring gantry.

In the illustrated embodiments, the radiation source 22 is a treatment radiation source for providing treatment energy. In other embodiments, in addition to being a treatment radiation source, the radiation source 22 can also be a diagnostic radiation source for providing diagnostic energy for imaging purpose. In such cases, the system 10 will include an imager 80, such as the imager 80, located at an operative position relative to the source 22 (e.g., under the support 14). In further embodiments, the radiation source 22 may be a treatment radiation source for providing treatment energy, wherein the treatment energy may also be used to obtain images. In such cases, in order to obtain imaging using treatment energies, the imager 80 is configured to generate images in response to radiation having treatment energies. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels and refer to energies that are used for treatment and diagnostic purposes, respectively. In some embodiments, the radiation source 22 is able to provide X-ray radiation at a plurality of photon energy levels within a range anywhere between approximately 10 keV and approximately 20 MeV. In further embodiments, the radiation source 22 can be a diagnostic radiation source. In such cases, the system 10 may be a diagnostic system with one or more moving parts. In the illustrated embodiments, the radiation source 22 is carried by the arm gantry 12. Alternatively, the radiation source 22 may be located within a bore (e.g., coupled to a ring gantry).

In the illustrated embodiments, the control system 18 includes a processing circuitry 54, such as a processor, coupled to an input/output device 40. The control system 18 may also include a monitor 56 for displaying data and an input device 58, such as a keyboard or a mouse, for inputting data. The operation of the radiation source 22 and the gantry 12 are controlled by the processing circuitry 54, which provides power and timing signals to the radiation source 22, and controls a rotational speed and position of the gantry 12, based on signals received from the processing circuitry 54. In some cases, the processing circuitry 54 may also control the radiation source 22 and the position of the patient support 14. In addition, in some cases, the processing circuitry 54 may be configured to control the beam 26 (e.g., beam hold for gating). Furthermore, the processing circuitry 54 may be configured to control an imaging process (e.g., triggering of imaging). Although the input/output device 40 is shown as a separate component from the gantry 12 and the processing circuitry 54, in alternative embodiments, the input/output device 40 can be a part of the processing circuitry 54.

During a treatment procedure, the source 22 rotates around the patient 20 and delivers treatment radiation beam from different gantry angles towards the patient 20. While the source 22 is at different gantry angles, the collimator 24 is operated to change the shape of the beam to correspond with a shape of the target tissue structure. For example, the collimator 24 may be operated so that the shape of the beam is similar to a cross sectional shape of the target tissue structure. In another example, the collimator 24 may be operated so that different portions of the target tissue structure receive different amount of radiation (as in an intensity-modulated radiation therapy (IMRT) procedure).

In other embodiments, the medical system 10 may be an imaging system configured to deliver imaging radiation beam towards the patient 20 for imaging the patient 20.

As shown in FIG. 1B, the system 10 also includes an optical system 150. The optical system 150 includes a light source 152, multiple cameras 154 (e.g., stereo cameras), and a processing unit 156 in communication with the cameras 154. In the illustrated example, the light source 152 is configured to provide structured light and/or non-structured light. Also, as shown in the figure, the optical system 150 has three cameras 154. In other embodiments, the optical system 150 may have fewer than three cameras 154 (e.g., one camera 154 or two cameras), or more than three cameras 154. Also, in other embodiments, the optical system 150 may include multiple light sources 152.

Also, in some embodiments, the structured light and/or non-structured light provided by the light source 152 may be in an infrared range (e.g., having infrared wavelength(s)). This technique obviates the need to use very intense light source(s), which may "blind" the patient, particularly during head, neck, and breast treatments in which the light is directed towards the upper part of the patient. In other embodiments, the light source 152 may be configured to provide non-visible light having other wavelengths (e.g., ultraviolet light). Also, use of non-visible light it does not exhibit stroboscopic effects that may confuse the patient, and it does not trigger symptoms of motion thickness.

The optical system 150 may also optionally include a frame 160 to which the cameras 154 and the light source 152 may be mounted. The frame 160 may be mounted to a ceiling and/or a wall of a room in which the medical system 10 is located. Alternatively, the frame 160 may be mounted to the medical system 10. The cameras 154 with the frame 160 may be preassembled at a factory, which allows easy installation at the medical facility. The cameras 154 may be moveably mounted to the frame 160. In one implementation, each of the cameras 154 may be rotatably mounted to the frame 160 (e.g., via a ball joint) so that the camera 154 is rotatable about one or more axes with respect to the frame 160. Similarly, the light source 152 may be moveably mounted to the frame 160. For example, the light source 152 may be rotatably mounted to the frame 160 (e.g., via a ball joint) so that the light source 152 is rotatable about one or more axes with respect to the frame 160. In other embodiments, instead of ball joints, the cameras 154 and the light source 152 may be moveably mounted to the frame 160 using other connectors, such as arms, so that the cameras 154 and the light source 152 are moveable with respect to the frame 160. In other embodiments, the one or more of the cameras 154 and/or the light source 152 may be mounted directly to the medical system 10 or a room.

Furthermore, in other embodiments, instead of having only one light source 152, the optical system 150 may include multiple light sources 152. In some embodiments, each of the light sources 152 may be configured to provide structured light and non-structured light. In other embodiments, one or more of the light sources 152 may be configured to provide structured light, while another one or more of the light sources 152 may be configured to provide non-structured light.

Also, in some embodiments, the light source 152 may be integrated with one or more cameras 154. For example, in one implementation, the optical system 150 may include multiple pods, wherein each pod may have one or more light sources 152 and one or more cameras 154 (e.g., two cameras 154).

As shown in FIG. 1B, the optical system 150 also includes a plurality of time-of-flight (TOF) cameras 158. Each TOF camera 158 is configured to provide depth image(s). A depth image has pixel values representing a distance between a reference point and a surface point detected. In some embodiments, each TOF camera 158 may be an infrared camera. During use, images from the cameras 154 and the TOF cameras 158 are processed by the processing unit 156 to obtain and monitor surface contours of the patient before and during treatment for the purpose of patient setup (absolute positioning and/or relative positioning), patient monitoring during treatment (e.g., monitoring absolute position and/or relative position), tool surveillance, prevention of patient-machine collisions, or a combination of the foregoing. Patient monitoring may include: (1) ensuring that the patient does not leave its setup position, and/or (2) recording a periodic patient motion due to breathing, and controlling a machine accordingly (e.g., beam hold, multi-leave collimator tracking, tracking of patient support, etc.).

In some cases, the TOF cameras 158 may help increase a field of view, and may observe blind spots not captured by the camera(s) 154.

In other embodiments, the optical system 150 may not include any TOF cameras 158.

In some embodiments, the optical system 150 may include multiple pods, wherein each pod may have one or more light sources 152, one or more cameras 154 (e.g., two cameras 154), and one or more TOF cameras 158. For example, there may be a first pod having one or more light sources 152 and two cameras 154, and a second pod having one or more light source 152 and two cameras 154. In addition, in some embodiments, a pod may include another type or auxiliary camera or depth measurement device. For example, apart from TOF camera, a pod may include ultrasonic distance sensor(s), light sensitive guard(s), or laser scanner(s). In some embodiments, a pod may also include one or more regular video camera(s). In such cases, a processor may obtain information from the regular video camera(s), and merge that information with 3D images. The video cameras may be used to detect markers with known geometric properties to obtain additional geometric 3D information. In further embodiments, the optical system 150 may include a web camera in each pod. In some cases, the image from the web camera or regular video camera may be overlaid on a detected surface or distance map. This may help to define a region of interest. For example, if a user does not see a surface representation of a user interface screen, but can see a realistic photograph of the scene, then the user may still define the region of interest using the user interface.

In some embodiments, the pod(s) may be mounted to a frame of the optical system 150. In other embodiments, the pod(s) may be mounted to a different frame than that of the optical system 150. Also, in further embodiments, the pod(s) may be configured to be mounted to the medical system 10, e.g., to the gantry, to the patient support. In some cases, the pod(s) may be mounted to deployable arms that are coupled to the medical system 10. In other embodiments, the pod(s) may be mounted to a room (e.g., to a wall, a ceiling, a floor, etc.).

The optical system 150 may be configured to provide patient setup, patient monitoring, device monitoring, respiratory motion control, patient-machine collision prevention, or any combination of the foregoing. Thus, in some cases, the same optical system 150 may provide multiple purposes. In some embodiments, different clinical use cases mentioned above may be performed simultaneously. In one implementation, the sequence of real-time input images from the camera(s) 154 and from the TOF camera(s) 158 may be processed by the processing unit 156 to patient monitoring and/or device monitoring. Also, in some embodiments, by combining external surface information of the patient (provided by the optical system 150) with x-ray imaging of the internal anatomy, highly integrated and automated treatment workflows may be achieved.

In one method of use, the light source 152 of the optical system 150 may be used to provide structured light. The structured light may be projected onto an object, such as a patient, for patient setup. As used in this specification, when light is described as being projected onto a patient, it is intended to cover the scenario in which the light is projected directly onto the patient (i.e., onto the skin of the patient), as well as the scenario in which the light is projected onto an object worn or coupled to the patient (e.g., onto a garment worn by the patient, a blanket covering the patient, a sticker on the patient, etc.). The cameras 154 sense the structured light as projected on the patient, and generate images of the projected structured light. The processing unit 156 is configured to process the images from the cameras 154, and determine a position (e.g., location and/or orientation) of the patient based on the processed images. Once the position of the patient is determined, the processing unit 156 may determine which direction to move the patient, and how much to move the patient, based on a desired position of the patient to be achieved.

In some cases, a reference image may be obtained by the processing unit 156. The reference image may be generated using the light source 152 and the cameras 154 during a treatment planning session, or on the day of treatment before the treatment session. The reference image includes an image of structured light as projected onto the patient, which indicates a desired position of the patient relative to some coordinate to be achieved. During the patient setup, the light source 152 and the cameras 154 are used to generate an input image. The processing unit 156 compares the input image with the reference image to determine if they match. If not, the patient is then positioned until the input image and the reference image match.

In some embodiments, if the optical system 150 includes one or more TOF cameras (e.g., the TOF cameras 158), the TOF camera(s) may generate one or more depth images. In such cases, the processing unit 156 may use the depth image(s) to perform patient setup. The processing unit 156 may use only the depth image(s) without the optical image(s) from the camera(s) 154. Alternatively, the processing unit 156 may use both depth image(s) and image(s) from the camera(s) 154 to perform patient setup. In one implementation, a reference depth image may be obtained by the processing unit 156. The reference depth image contains information regarding a desired position of a surface of a patient with respect to one or more objects (e.g., a component of the medical system 10, the patient support 14, a wall of the room, etc.) surrounding the patient. The reference depth image may be generated by the TOF camera(s) during a treatment planning session, or on the day of the treatment before the treatment session begins. During a patient setup procedure, the TOF camera(s) provides depth image, which indicates a position of the surface of the patient with respect to one or more objects surrounding the patient. The processing unit 156 compares the depth image with the reference depth image to see if they match. If not, then the patient is positioned until the depth image matches the reference depth image.

Additional functions performed by the medical system 10 are described in U.S. application Ser. No. 15/728,475, the entire contents of which are incorporated by reference.

In other embodiments, the light source 152 provides structured light and directs it onto an object, and the reflected light (e.g., IR light) from the object is measured by image sensors of two lenses of a camera 154 (e.g., a stereo camera) which are offset from the light source 152. The geometry of the light source 152 and the two lenses is known. Accordingly, the processing unit 156 can use triangulation to calculate the distance of surface by finding the same structured pattern in the images from image sensors. The result is a depth map (or distance map), similar to the TOF technology.

In some cases, the light source 152 and the two cameras 154 may be implemented as one pod, and there may be additional pod(s), wherein each pod has a light source and two offset cameras. The processing unit 156 may be configured to add the depth map from one pod to other depth map(s) determined from other pod(s) at other locations in order to map out the surface of the object, thereby forming a larger depth map. In some cases, this depth map may be represented by a point cloud in a defined coordinate system. The processing unit 156 may also calculate the distance of a reference surface to a measured surface to detect a possible offset.

In some embodiments, the structured pattern may be implemented using time-varying gray levels. In such cases, the time-varying gray levels are projected by a light source on the surface to be measured. The processing unit 156 then utilizes an algorithm to find the corresponding pixel in both camera images. Knowing the camera pixel for this surface point and the cameras configuration (e.g., position and/or orientation of each camera in the pod), the angle of the ray towards this object point can be determined by the processing unit 156 for each camera. As the distance between both cameras in the pod is known, triangulation technique may then be used by the processing unit 156 to calculate the distance to this surface point (also known as "distance of surface"). In some embodiments, such distance to the surface point may be measured from the camera pod. The above process may be repeated for all object points to thereby create a depth/distance map, which represents a surface of interest in a known coordinate system.

In one implementation, each of the cameras in a given pod (or image sensors in a single camera) records a series of images with different fringe patterns projected onto the patient/object of interest. From those images, a disparity map is then created by the processing unit 156. A disparity map measures the distance of two corresponding points as seen by the two cameras. These disparity maps are then used by the processing unit 156 to create a 3D ordered point cloud, i.e. a surface information of the object that is seen by both cameras (in a given coordinate system). With multiple pods, such 3D ordered point clouds may be merged to a bigger common surface by the processing unit 156. The bigger common surface is advantageous because it fills gaps of areas that are not seen by one or several pods, and it can increase the overall field of view.

In another implementation, before a treatment session, images of the structured light as projected onto the patient may be generated and recorded as a 4D patient surface.

The optical system 150 may be configured to provide patient setup, patient monitoring, device monitoring, respiratory motion control, patient-machine collision prevention, or any combination of the foregoing. Also, in some embodiments, by combining external surface information of the patient (provided by the optical system 150) with x-ray imaging of the internal anatomy, highly integrated and automated treatment workflows may be achieved.

Conventionally, in a surface-based monitoring workflow, a user manually defines a region-of-interest (ROI) on a 3D surface image of a patient. The ROI is used by a radiation treatment system (e.g., radiotherapy system) to measure motion such as respiratory motion.

As shown in FIG. 1A, the control system 18 may communicate with a user interface device 90. The user interface device 90 may be implemented using a computer, a tablet, a smart phone, or any of other handheld device. The user interface device 90 includes a screen 92 to display information provided to the user interface device 90 from the control system and processing circuitry 95 to control the screen 92 to display a user interface. The communication between the interface device 90 and the control system 18 may follow any suitable wired or wireless communication standards or protocols such as Universal Mobile Telecommunications System (UMTS), long term evolution (LTE), LTE-Advanced (LTE-A), the fifth generation (5G) New Radio (NR), Wireless Fidelity (Wi-Fi) and Worldwide Interoperability for Microwave Access (WiMAX) standards, and employ any suitable communication technologies, including, for example, Multiple-Input Multiple-Output (MIMO), Orthogonal Frequency Division Multiplexing (OFDM), time division multiplexing (TDM), frequency division multiplexing (FDM), code division multiplexing (CDM), Bluetooth, ZigBee, and machine type communication (MTC), enhanced mobile broadband (eMBB), massive machine type communication (mMTC), ultra-reliable low latency communication (URLLC), Carrier Aggregation (CA), Dual Connection (DC), New Radio Unlicensed (NR-U) technologies.

The processing circuitry 95 of the user interface device is configured to cause the tablet to display information from the optical surface monitoring system. The processing circuitry 95 is also configured to control different workflow steps (e.g. start the breathing analysis phase, define the monitoring ROI if the user does not approve of the system proposal) based on input from the user.

Figure 2:
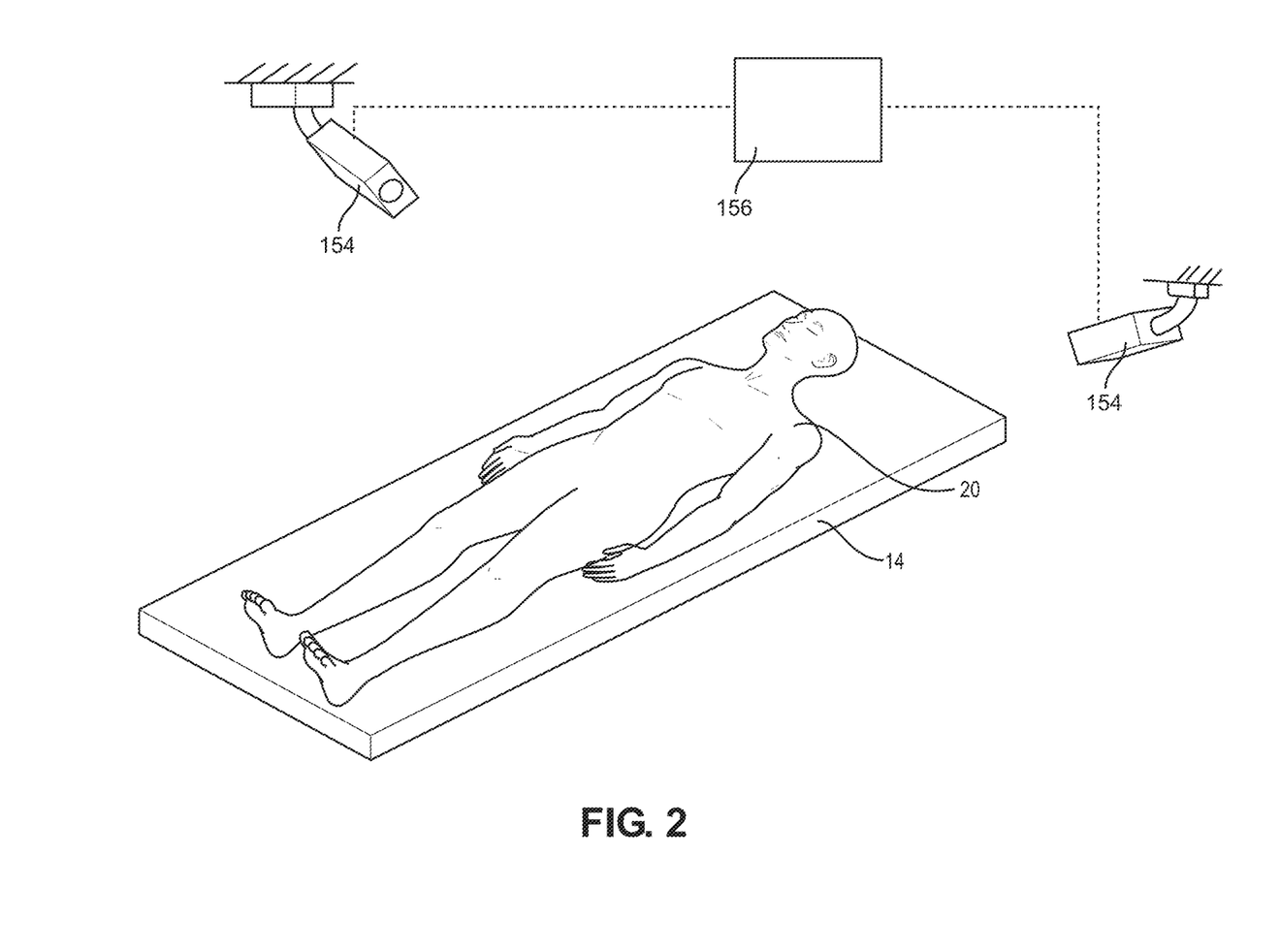
FIG. 2 illustrates an example embodiment of a medical system including two stereo cameras.

FIG. 2 illustrates an example embodiment of a medical system including two stereo cameras configured to produce a 3D patient surface image (e.g., as shown in FIG. 8A). In the example where the cameras are stereo cameras and the number of stereo cameras 154 is two, a surface model of the patient may be formed by combining point clouds from the different cameras 154. The two stereo cameras 154 may be positioned to view opposite sides of a patient 20. In particular, there is a first stereo camera 154 positioned to view the patient 20 from his/her right side, and a second stereo camera 154 positioned to view the patient 20 from his/her left side. In another example, there may be a first camera 154 positioned to view the patient 20 from above his/her head towards a direction of the feet, and a second camera 154 positioned to view the patient from below his/her feet towards a direction of the heard. In some embodiments, the processing unit 156 may be configured to receive a first image (e.g., with first depth information) from the first stereo camera 154, and to receive a second image (e.g., with second depth information from the second stereo camera 154. Because the relative position between the two stereo cameras 154 is known, the processing unit 156 may use this positional information to perform coordinate transformation so that the surfaces of the patient 20 from the two images may be combined to form a 3D surface image of the patient.

Similarly, the processing unit 156 and/or processing circuitry 54 may determine a transformation between a frame of reference of the stereo camera and a frame of reference of the radiation source (e.g., LINAC).

In some embodiments, the processing unit 156 may be configured to determine motion of a surface from the point cloud of the entire field of view of a stereo camera 154, or a merged multi-camera view based on expected and/or detected protected surface location and dimension. If the system includes multiple cameras 154, the multiple cameras may be calibrated to align the cameras to produce a merged view.

In some embodiments, the processing unit 156 may generate the motion values as described in Geng, *Structured-light 3D surface imaging: a tutorial*, Advances in Optics and Photonics, Vol. 3, Issue 2, pp. 128-160 (2011), the entire contents of which are incorporated by reference.

Figure 3:
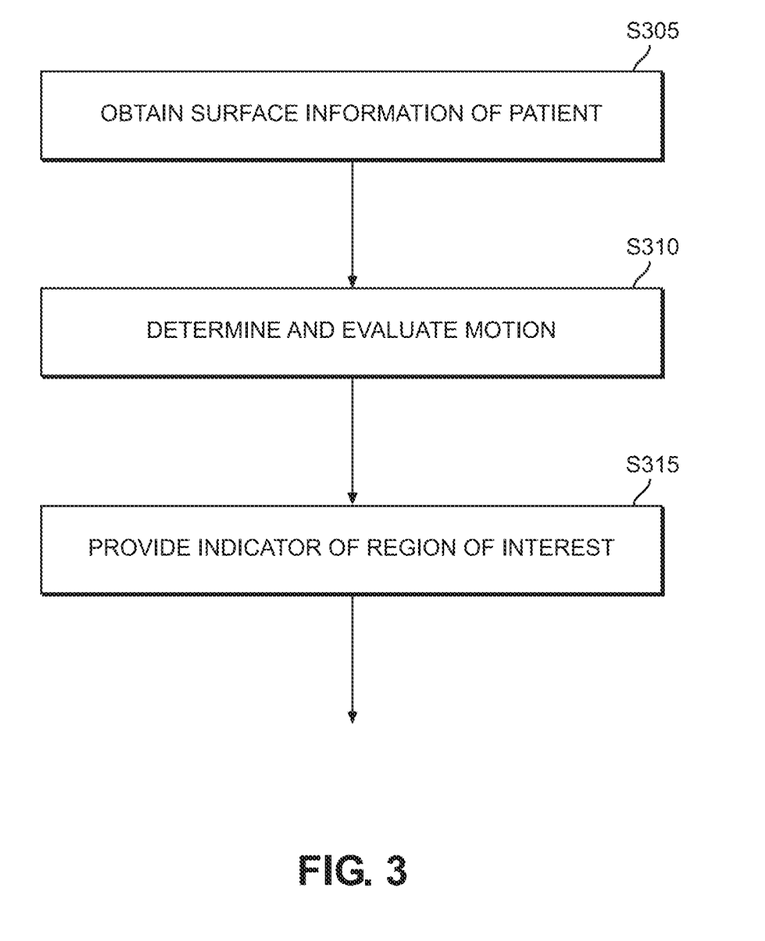
FIG. 3 illustrates a method of displaying a motion of a patient according to an example embodiment.

FIG. 3 illustrates a method of displaying a motion of a patient according to an example embodiment. The method of FIG. 3 may be performed by a medical system such as the medical system 10. The calculations and algorithms described with reference to FIG. 3 may be performed by a control system such as the control system 18. More specifically, processing circuitry within the control system is configured to cause the medical system to perform the functions described herein. If the processing circuitry is a processor, the processor is configured to cause the medical system to perform the functions described herein by executing instructions stored in memory.

At S305, the control system obtains surface information of the patient, e.g., a patient surface. For example, the control system obtains a 4D point cloud of the patient surface over a particular period of time (a learning phase) by combining multiple 3D point clouds produced by the 3D stereo cameras over the period of time.

The particular period of time may be sufficient to cover a plurality of breathing cycles such as 4-5 breathing cycles. In other embodiments, the particular period of time may be longer to cover more breathing cycles. In other embodiments, the particular period of time may be shorter to cover less breathing cycles.

In some embodiments, the particular period of time is a sufficient time for the control system to obtain information regarding a phase of a breathing sample of the patient, and not just the amplitude. For example, during a 4D CT acquisition, a 4D CT may be grouped into 10 3D CTs, with each 3D CT representing a different phase within the breathing cycle.

In other embodiments, e.g., for DIBH, the particular period of time is set to obtain on the amplitude.

The 4D point cloud may be associated with measurements of multiple regions of the surface of the patient. For example, the control system may obtain a first motion signal from a first area of the patient and a second motion signal from a second area of the patient.

The first and second areas correspond to potential ROIs. The potential ROIs may be defined by the control system based on patient treatment information (e.g., as set forth in DICOM RT). The ROI may be also be defined in accordance with U.S. application Ser. No. 17/854,581, filed on the same day herewith, entitled "Methods, Systems and Computer Readable Mediums for Determining a Region-of-Interest in Surface-Guided Monitoring", the entire contents of which are incorporated herein by reference.

In other example embodiments, the potential ROI areas are set manually.

The motion information is used to find and define the correct ROI areas (e.g., chest and abdomen).

At S310, the control system determines a motion of the patient based on the surface information. The control system may begin to monitor the motion of particular regions of the surface of the patient when the patient is placed on the couch. The particular regions (e.g., possible regions of interest) the control system monitors are based on a clinical protocol (e.g., CT imaging directives and or instructions from a physician. As an example, for assessing respiratory motion, the control system monitors an upper thorax (chest) area and an abdomen area of the surface of the patient. The control system may monitor vertical amplitude changes in the particular regions.

During the monitoring, the control device may provide the vertical amplitude changes to the user interface device (e.g., the user interface device 90). More specifically, the control device provides the user interface device with a first motion map (e.g., a heat map) corresponding to measurements in the surface information and changing over time based on the measurements in the surface information. The user interface device may display the first motion map, as shown in FIG. 4.

Figure 4:
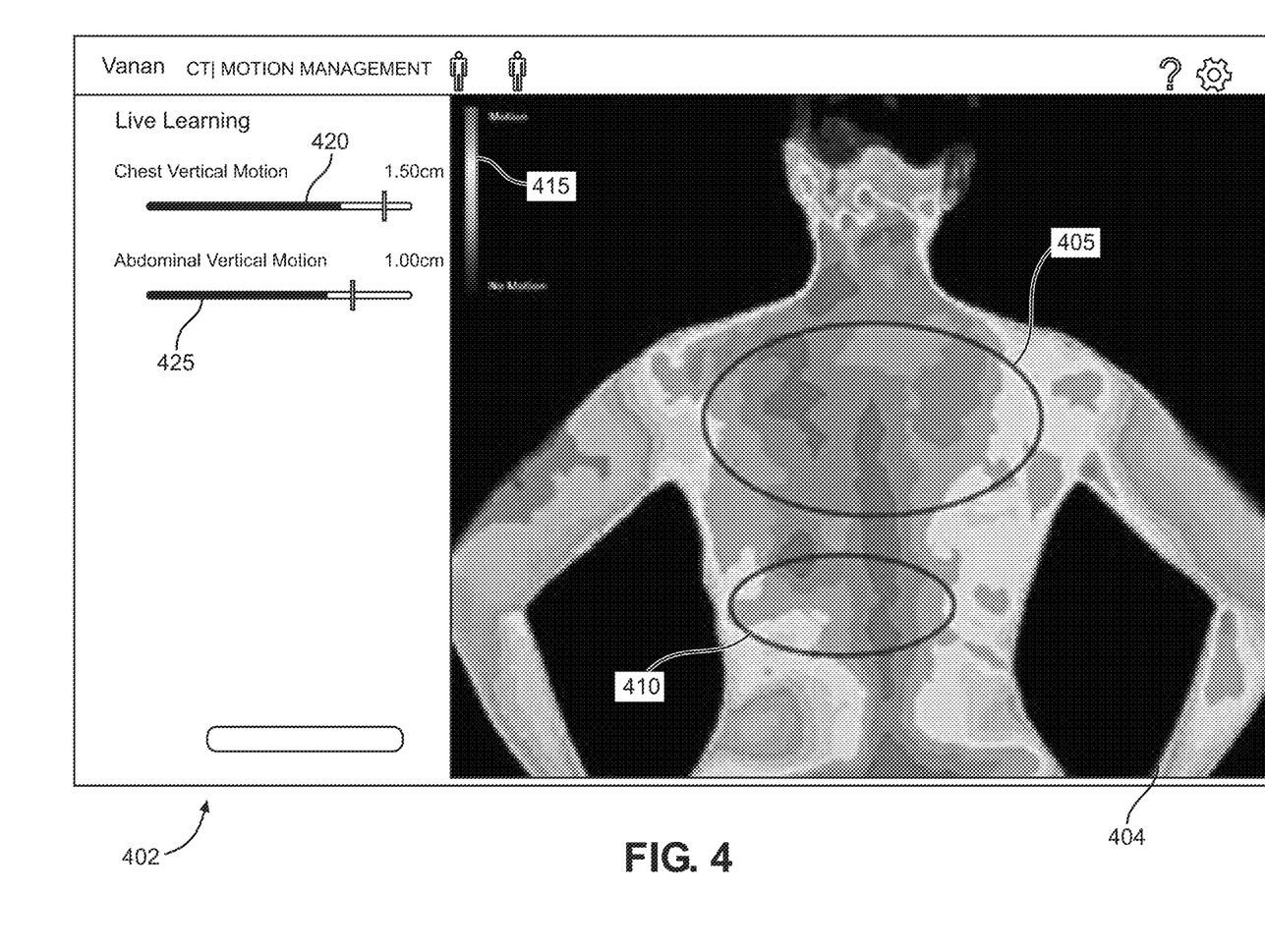
FIG. 4 illustrates a user interface according to an example embodiment.

FIG. 4 illustrates a user interface according to an example embodiment.

A portion of user interface 402 displays a heat map 404 of the measured motion. The shape of the heat map corresponds to a position of the patient during treatment and/or imaging.

In the example of FIG. 4, two particular areas are identified as possible regions of interest. More specifically, the example shown in FIG. 4 is for assessing respiratory motion. Thus, the user interface device provides an outline for an upper thorax (chest) area 405 and an outline for an abdomen area 410 of the surface of the patient. Another portion of the user interface 402 provides a key 415 for indicating a level of motion associated with each shade.

Another portion 420 of the user interface 402 displays an average vertical motion within the area 405 and another portion 425 of the user interface 402 displays an average vertical motion within the area 410. The portions 420 and 425 are live images because the portions 420 and 425 may change as the motion information is being obtained by the control system.

Figure 7A:
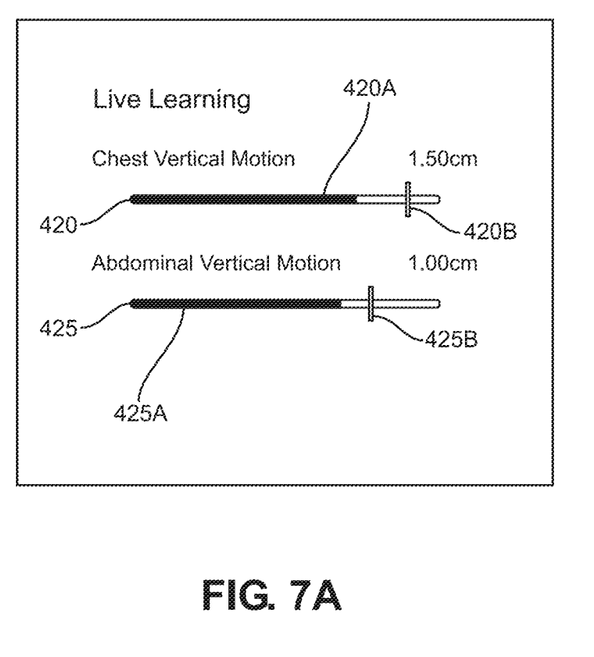
FIG. 7A illustrates a zoomed-in area of the user interface of FIG. 4.

FIG. 7A illustrates zoomed-in view of the portions 420 and 425. The portion 420 includes horizontal bar 420a that indicates the real-time average motion of the area 405 and a vertical line 420b that indicates the maximum average motion of the area 405 that has occurred during the particular period of time. The portion 425 includes horizontal bar 425a that indicates the real-time average motion of the area 410 and a vertical line 425b that indicates the maximum average motion of the area 410 that has occurred during the particular period of time.

The control system determines the real-time average motion of a particular area by averaging an amplitude change between sampling points in the particular area over the sampling period (i.e., the particular period of time).

Moreover, during S310, the control system determines an average vertical amplitude change for each point of the 3D patient surface during the particular period of time. The particular period of time may also be referred to as a learning phase.

Figure 5:
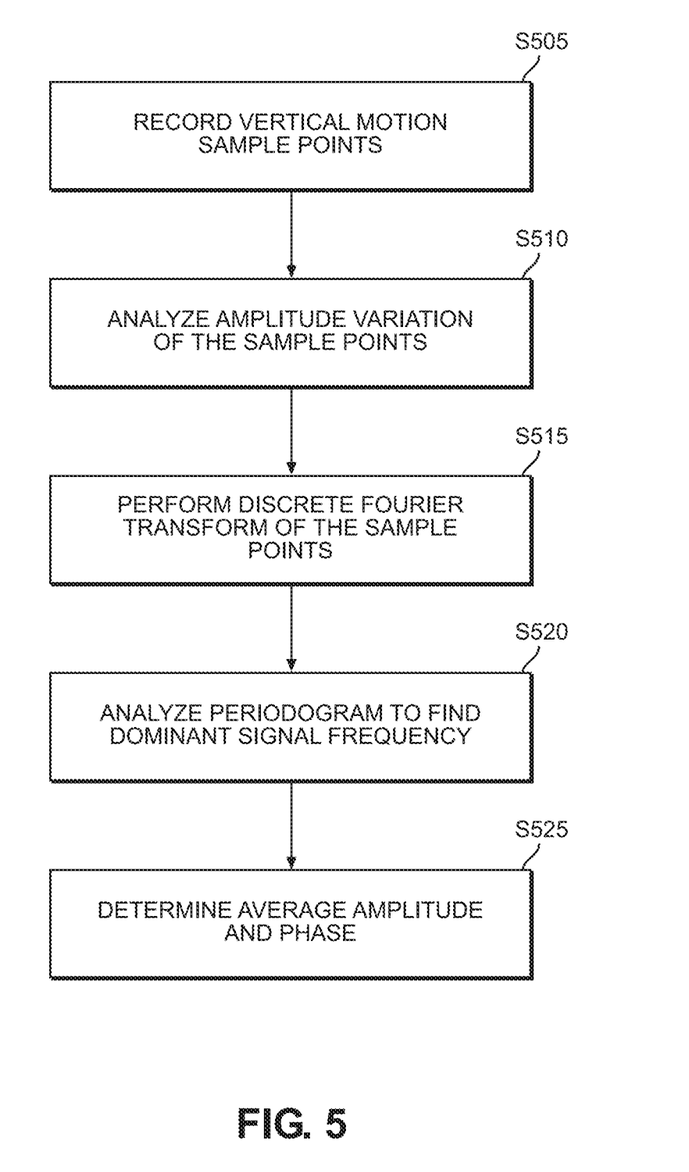
FIG. 5 illustrates an example embodiment of determines an average vertical amplitude change for each point of the 3D patient surface.

FIG. 5 illustrates an example embodiment of determines an average vertical amplitude change for each point of the 3D patient surface.

At S505, the control system stores vertical motion sample points over the period of time. In some embodiments, the sampling frequency may be 20-30 Hz, but is not limited thereto.

At S510, the control system determines and analyzes variations in amplitude of the sampled points. For example, the controller system determines changes in amplitude between sampled points of the region.

At S515, the control system performs a Discrete Fourier Transform (DPI') of the sampled points to generate a periodogram of the sampled data points. At S520, the control system analyzes the periodogram to determine a dominant signal frequency.

At S525, the control system determines an average amplitude and phase from the dominant signal frequency. The control system may use known methods such as—peak-search. The average phase provides a breathing frequency of the patient.

Referring back to FIG. 3, the control system provides an indicator of a region of interest to the user interface device at S315. During S315, the control system determines a region of interest of the patient based on the motion determined motion and provides the determined region of interest to the user interface device. More specifically, the control system may determine a region of interest from the average vertical amplitude change for each point of the 3D patient surface determined at S310.

In some example embodiments, the ROI determined by the control system is based on the motion intensity such as a point or an area of multiple points having a highest motion (movement) value. In other example embodiments, the ROI determined by the control system is also based on patient anatomy information and/or landmarks detected on the point cloud (e.g., a anatomy landmark being a 10 cm×10 cm area placed between the points where the arms branch off from the torso).

For example, the control system may compare a motion signal from the area 405 to a motion signal from the area 410. The motion signal from the area 405 represents the average motion change over the particular period of time for the area 405 and the motion signal from the area 410 represents the average motion change over the particular period of time for the area 410.

In some embodiments, the control system determines the area associated with the highest average motion over the particular period of time as the ROI of the patient.

Additionally, the control system may determine the ROI further based on at least one of a signal-to-noise-ratios (SNR) or a contrast-to-noise-ratios (CNR) of the particular areas. For example, a high SNR relative to SNR values in other areas of the image and indicates strong breathing motion and only little 'noise' from other motion. The control system may determine the ROI to be an area with the highest SNR.

The control device communicates an average motion heat map and ROI to the user interface device (e.g., an indicator of the ROI). More specifically, the control device provides the user interface device with an average motion map (e.g., an average motion heat map) depicting an average motion of the patient. The average motion map is a static map and includes a ROI. The user interface device may display the average motion map, as shown in FIG. 6.

Figure 6:
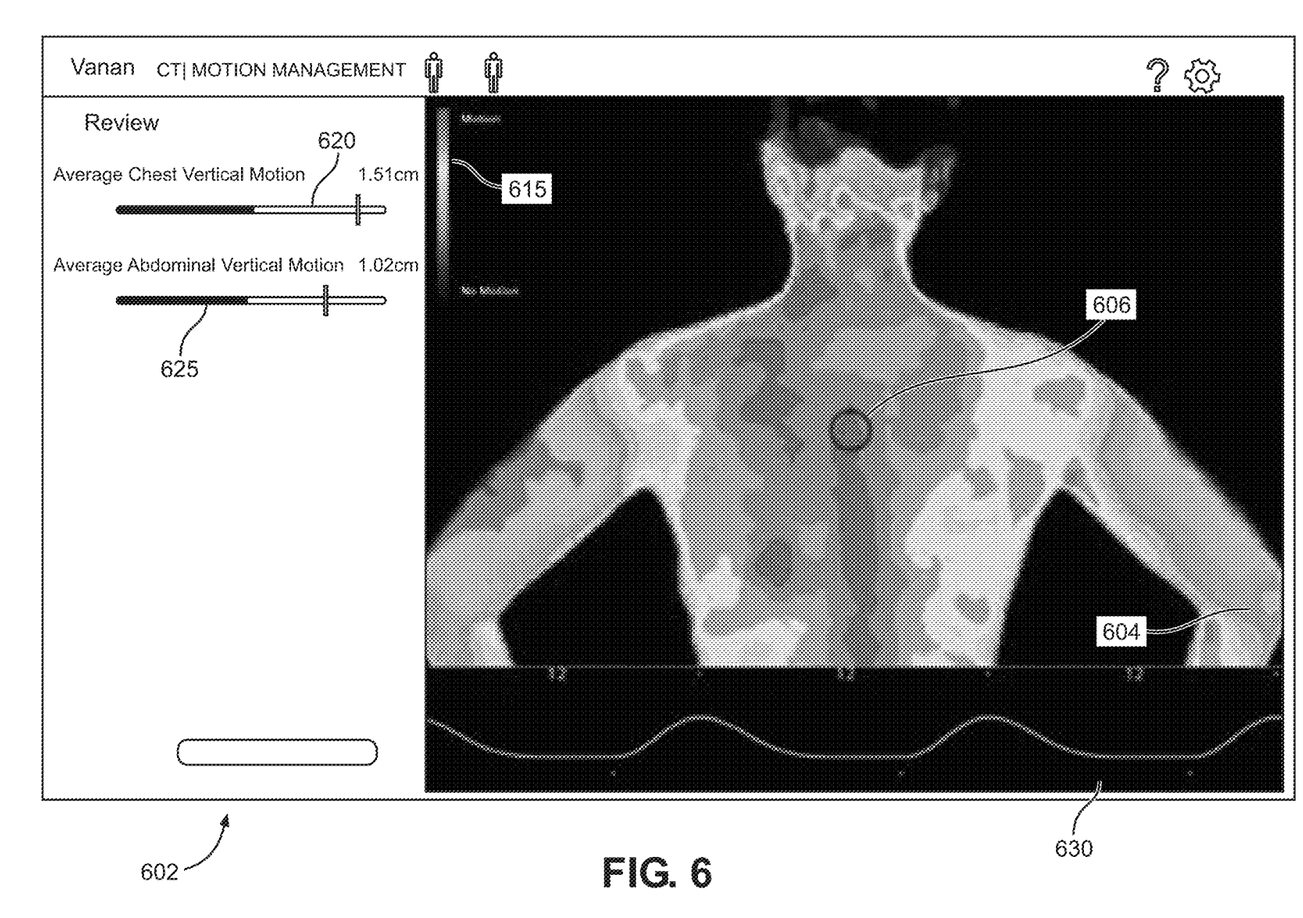
FIG. 6 illustrates a user interface according to an example embodiment.

The user interface device may display the average change in vertical amplitude in real time, as shown in FIG. 6.

FIG. 6 illustrates a user interface according to an example embodiment.

A portion of user interface 602 displays a heat map 604 of the measured motion. The shape of the heat map corresponds to a position of the patient during treatment and/or imaging.

Using the ROI indicator from the control system, the user interface device causes user interface 602 to display an outline 606 corresponding to the ROI determined by the control system. Another portion of the user interface 602 provides a key 615 for indicating a level of motion associated with each shade.

Another portion 620 of the user interface 602 displays an average vertical motion within the area 405 and another portion 625 of the user interface 602 displays an average vertical motion within the area 410. The portions 620 and 625 are static images because the portions 620 and 625 are displayed by the user interface device after the particular period of time obtaining motion information of the patient.

Figure 7B:
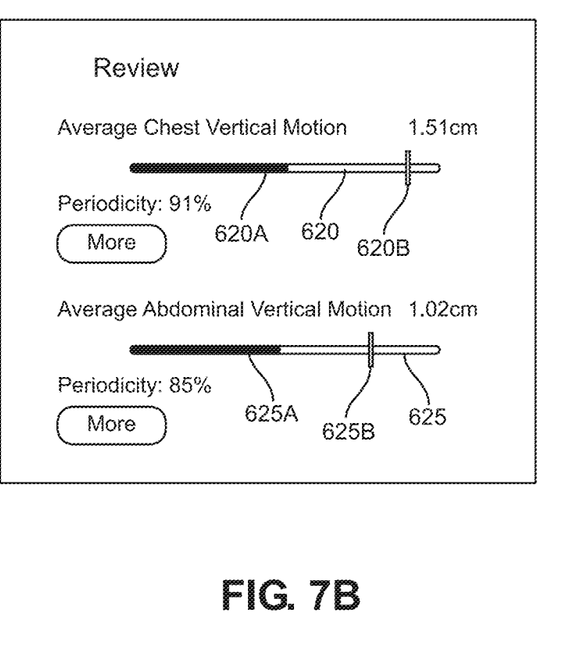
FIG. 7B illustrates a zoomed-in area of the user interface of FIG. 6.

FIG. 7B illustrates zoomed-in view of the portions 620 and 625. The portion 620 includes horizontal bar 620a that indicates the average motion of the ROI 606 and a vertical line 620b that indicates the maximum average motion of the ROI 606 that occurred during the particular period of time.

The portion 625 includes horizontal bar 625a that indicates the real-time average motion of the area 410 and a vertical line 625b that indicates the maximum average motion of the area 410 that has occurred during the particular period of time.

Referring back to FIG. 6, another portion 630 of the user interface 602 displays live motion information measured within the ROI 606. In some example embodiments, the another portion 630 displays a waveform representing vertical movement within the ROI 606. Thus, while the heat map 604 illustrates information captured during the first period of time, the another portion 630 displays live motion information the occurs after the first period of time.

While the heat maps are shown in shades of gray to encode respiratory motion, it should be understood that shades of colors may be used to show changes in motion. The visualization allows to easily detect those body areas that move most due to the patients respiration. It also allows to distinguish, whether the patient is breathing with the chest or with the belly/diaphragm. This has clinical relevance as it comes to deep-inspiration breath-hold CT acquisition or RT treatment. The visualization would also allow to clip motion that is below or above a certain threshold which could help the user while reviewing the information. The colors of the map could also be mapped to either a relative scale (red=max value per acquired frame) or an absolute scale (red=5 cm of amplitude).

As described above, the control system converts surface information (e.g., 3D point cloud) and converts the 3D/4D information into a two-dimensional (3D) motion map (e.g., the first motion map and the average motion map).

Figure 8:
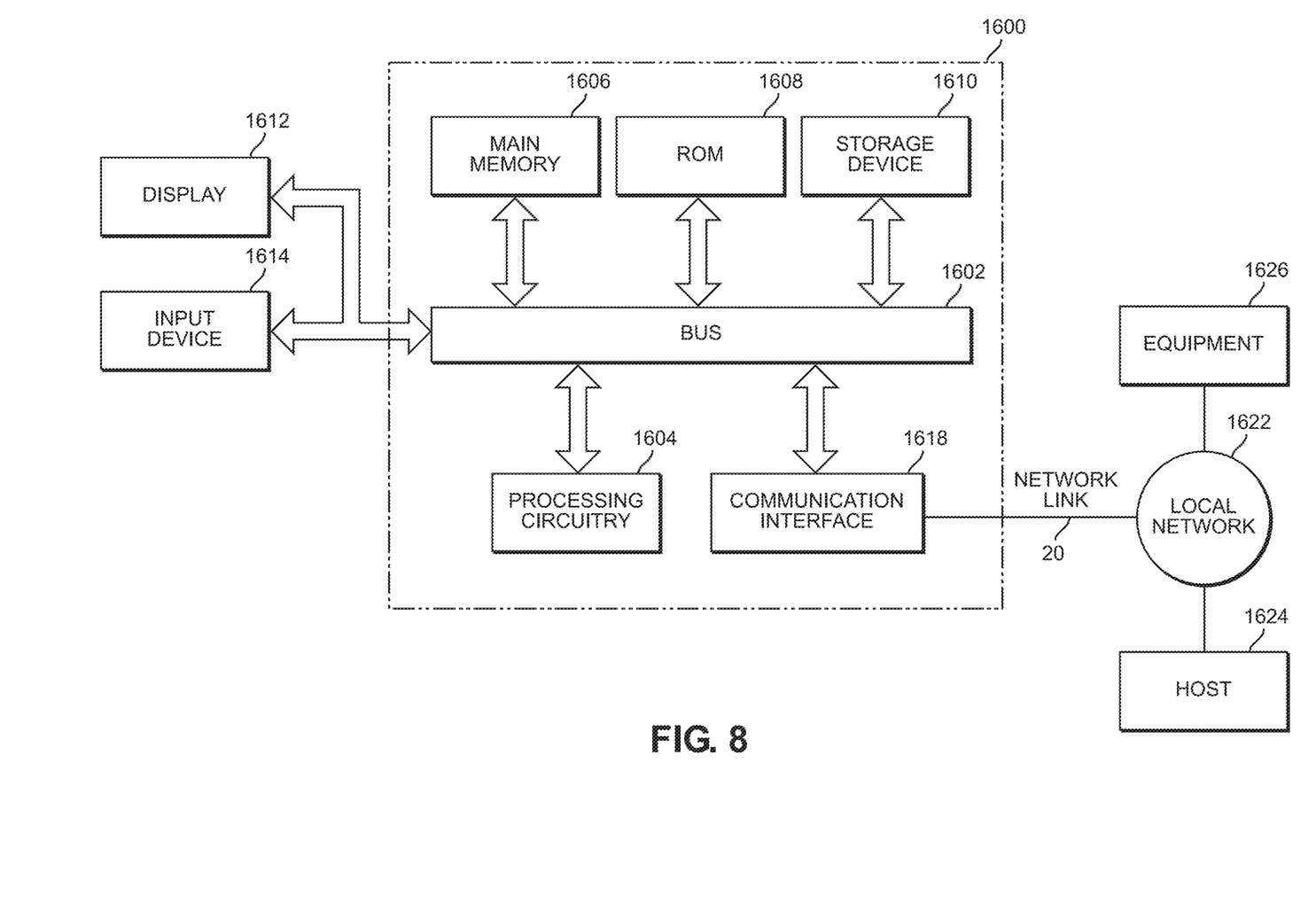
FIG. 8 illustrates a diagram of a control system with which embodiments may be implemented.

FIG. 8 is a block diagram illustrating an embodiment of a specialized control system 1600 that can be used to implement various embodiments described herein. For example, the control system 1600 may be configured to display the user interface in accordance with example embodiments.

Also, in some embodiments, the control system 1600 may be used to implement the processing circuitry 54, the processing unit 156 or processing circuitry in the user interface device 90. The control system 1600 may also be an example of any control system described herein.

The control system 1600 includes a bus 1602 or other communication mechanism for communicating information, and processing circuitry 1604 (e.g., at least one processor and/or ASIC) coupled with the bus 1602 for processing information. In examples where the processing circuitry 1604 is hardware configured to executed stored instructions (e.g., a processor), the control system 1600 also includes a main memory 1606, such as a random-access memory (RAM) or other dynamic storage device, coupled to the bus 1602 for storing information and instructions to be executed by the processing circuitry 1604. The main memory 1606 also may be used for storing temporary variables or other intermediate information during execution of instructions to be executed by the processing circuitry 1604. The control system 1600 further includes a read only memory (ROM) 1608 or other static storage device coupled to the bus 1602 for storing static information and instructions for the processing circuitry 1604. A data storage device 1610, such as a magnetic disk or optical disk, may be provided and coupled to the bus 1602 for storing information and instructions.

The control system 1600 may be coupled via the bus 1602 to a display 1612, such as a flat panel, for displaying information to a user. An input/output device 1614, such as a touchscreen, is coupled to the bus 1602 for communicating information and command selections to processing circuitry 1604. Another type of user input device is cursor control 1616, such as a mouse, a trackball, or cursor direction keys for communicating direction information and command selections to processing circuitry 1604 and for controlling cursor movement on display 167. This input device typically has two degrees of freedom in two axes, a first axis (e.g., x) and a second axis (e.g., y), that allows the device to specify positions in a plane.

While the display 1612 and I/O device 1614 are shown outside of the control system 1600, it should be understood that the display 1612 and the I/O device 1614 are part of the control system 1600 such as shown in FIG. 9.

In some embodiments, the control system 1600 can be used to perform various functions described herein. According to some embodiments, such use is provided by control system 1600 in response to the processing circuitry 1604 executing one or more sequences of one or more instructions contained in the main memory 1606. Those skilled in the art will know how to prepare such instructions based on the functions, algorithms and methods described herein. Such instructions may be read into the main memory 1606 from another processor-readable medium, such as storage device 1610. Execution of the sequences of instructions contained in the main memory 1606 causes the processing circuitry 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

Transmission media includes coaxial cables, copper wire and fiber optics, including the wires that comprise the bus 1602. Transmission media can also take the form of acoustic or light waves, such as those generated during radio wave and infrared data communications.

Various forms of processor-readable media may be involved in carrying one or more sequences of one or more instructions to the processing circuitry 1604 for execution. For example, the instructions may initially be carried on a magnetic disk of a remote computer. The remote computer can load the instructions into its dynamic memory and send the instructions over a network, such as the Internet or a local network. A receiving unit local to the control system 1600 can receive the data from the network and provide the data on the bus 1602. The bus 1602 carries the data to the main memory 1606, from which the processing circuitry 1604 retrieves and executes the instructions. The instructions received by the main memory 1606 may optionally be stored on the storage device 1610 either before or after execution by the processing circuitry 1604.

The control system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the control system 1600, are exemplary forms of carrier waves transporting the information. The control system 1600 can send messages and receive data, including program code, through the network(s), the network link 1620, and the communication interface 1618.

Although the terms first, second, etc. may be used herein to describe various elements, these elements should not be limited by these terms. These terms are only used to distinguish one element from another. For example, a first element could be termed a second element, and similarly, a second element could be termed a first element, without departing from the scope of this disclosure. As used herein, the term "and/or," includes any and all combinations of one or more of the associated listed items.

When an element is referred to as being "connected," or "coupled," to another element, it can be directly connected or coupled to the other element or intervening elements may be present. By contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Specific details are provided in the following description to provide a thorough understanding of example embodiments. However, it will be understood by one of ordinary skill in the art that example embodiments may be practiced without these specific details. For example, systems may be shown in block diagrams so as not to obscure the example embodiments in unnecessary detail. In other instances, well-known processes, structures and techniques may be shown without unnecessary detail in order to avoid obscuring example embodiments.

As discussed herein, illustrative embodiments will be described with reference to acts and symbolic representations of operations (e.g., in the form of flow charts, flow diagrams, data flow diagrams, structure diagrams, block diagrams, etc.) that may be implemented as program modules or functional processes include routines, programs, objects, components, data structures, etc., that perform particular tasks or implement particular abstract data types and may be implemented using existing hardware, for example, processing or control circuitry such as, but not limited to, one or more processors, one or more Central Processing Units (CPUs), one or more controllers, one or more arithmetic logic units (ALUs), one or more digital signal processors (DSPs), one or more microcomputers, one or more field programmable gate arrays (FPGAs), one or more System-on-Chips (SoCs), one or more programmable logic units (PLUs), one or more microprocessors, one or more Application Specific Integrated Circuits (ASICs), or any other device or devices capable of responding to and executing instructions in a defined manner.

Although a flow chart may describe the operations as a sequential process, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "memory," "storage medium," "processor readable medium," "computer readable storage medium" or "non-transitory computer readable storage medium" may represent one or more devices for storing data, including read only memory (ROM), random access memory (RAM), magnetic RAM, core memory, magnetic disk storage mediums, optical storage mediums, flash memory devices and/or other tangible machine-readable mediums for storing information. The term "computer-readable medium" may include, but is not limited to, portable or fixed storage devices, optical storage devices, and various other mediums capable of storing, containing or carrying instruction(s) and/or data.

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, a processor or processors will perform the necessary tasks. For example, as mentioned above, according to one or more example embodiments, at least one memory may include or store computer program code, and the at least one memory and the computer program code may be configured to, with at least one processor, cause a network element or network device to perform the necessary tasks. Additionally, the processor, memory and example algorithms, encoded as computer program code, serve as means for providing or causing performance of operations discussed herein.

The terms "including" and/or "having," as used herein, are defined as comprising (i.e., open language). The term "coupled," as used herein, is defined as connected, although not necessarily directly, and not necessarily mechanically. Terminology derived from the word "indicating" (e.g., "indicates" and "indication") is intended to encompass all the various techniques available for communicating or referencing the object/information being indicated. Some, but not all, examples of techniques available for communicating or referencing the object/information being indicated include the conveyance of the object/information being indicated, the conveyance of an identifier of the object/information being indicated, the conveyance of information used to generate the object/information being indicated, the conveyance of some part or portion of the object/information being indicated, the conveyance of some derivation of the object/information being indicated, and the conveyance of some symbol representing the object/information being indicated.

According to example embodiments, medical systems, may be (or include) hardware, firmware, hardware executing software or any combination thereof. Such hardware may include processing or control circuitry such as, but not limited to, one or more processors, one or more CPUs, one or more controllers, one or more ALUs, one or more DSPs, one or more microcomputers, one or more FPGAs, one or more SoCs, one or more PLUs, one or more microprocessors, one or more ASICs, or any other device or devices capable of responding to and executing instructions in a defined manner.

Benefits, other advantages, and solutions to problems have been described above with regard to specific embodiments. However, the benefits, advantages, solutions to problems, and any element(s) that may cause or result in such benefits, advantages, or solutions, or cause such benefits, advantages, or solutions to become more pronounced are not to be construed as a critical, required, or essential feature or element of any or all the claims.

What is claimed is:

1. A method comprising:
    obtaining surface information of a patient using a camera;
    determining a motion of the patient based on the surface information; and
    providing an indicator of a region of interest (ROI) of the patient based on the motion, wherein
        the providing the indicator includes determining the ROI of the patient based on the motion, and
        the ROI corresponds to an area of the patient having a highest movement value.

2. The method of claim 1, wherein the obtaining the surface information includes,
    obtaining a first motion signal from a first area of the patient, and
    obtaining a second motion signal from a second area of the patient, the ROI being based on the first motion signal and the second motion signal.

3. The method of claim 1, wherein the determining the ROI is based on at least one of
    a signal-to-noise ratio associated with a first area of the patient, or
    a contrast-to-noise ratio between a movement in the first area and a static area of the patient.

4. The method of claim 1, wherein the determining the motion includes,
    providing a first motion map of the patient before displaying the indicator, the first motion map corresponding to measurements in the surface information and changing over time based on the measurements in the surface information.

5. The method of claim 4, wherein
the determining the motion of the patient includes,
   determining an average motion of the patient based on the measurements in the surface information, the average motion being an average vertical change, and
the providing the indicator includes,
   displaying an average motion map after displaying the first motion map, the average motion map depicting the average motion of the patient, the average motion map being a static map and the average motion map including the ROI, and
   displaying the indicator over the ROI of the patient in the average motion map.

6. The method of claim 5, wherein the surface information is a three-dimensional (3D) point cloud and the displaying the indicator of the ROI of the patient displays the indicator on a two-dimensional (2D) motion map.

7. An apparatus comprising:
processing circuitry configured to cause the apparatus to,
   obtain surface information of a patient using a camera,
   determine a motion of the patient based on the surface information,
   determine a region of interest (ROI) of the patient based on the motion, the ROI corresponding to an area of the patient having a highest movement value, and
   provide an indicator of the ROI of the patient based on the motion.

8. The apparatus of claim 7, wherein the processing circuitry is configured to cause the apparatus to,
   obtain a first motion signal from a first area of the patient, and
   obtain a second motion signal from a second area of the patient, the ROI being based on the first motion signal and the second motion signal.

9. The apparatus of claim 7, wherein the processing circuitry is configured to cause the apparatus to determine the ROI based on at least one of
   a signal-to-noise ratio associated with a first area of the patient, or
   a contrast-to-noise ratio between a movement in the first area and a static area of the patient.

10. The apparatus of claim 7, wherein the processing circuitry is configured to cause the apparatus to,
   provide a first motion map of the patient before displaying the indicator, the first motion map corresponding to measurements in the surface information and changing over time based on the measurements in the surface information.

11. The apparatus of claim 10, wherein the processing circuitry is configured to cause the apparatus to,
   determine an average motion of the patient based on the measurements in the surface information, the average motion being an average vertical change,
   display an average motion map after displaying the first motion map, the average motion map depicting the average motion of the patient, the average motion map being a static map and the average motion map including the ROI, and
   display the indicator over the ROI of the patient in the average motion map.

12. The apparatus of claim 11, wherein the surface information is a three-dimensional (3D) point cloud and the displaying the indicator of the ROI of the patient displays the indicator on a two-dimensional (2D) motion map.

* * * * *